US009027557B2

(12) United States Patent
Dussart et al.

(10) Patent No.: US 9,027,557 B2

(45) Date of Patent: May 12, 2015

(54) ELASTIC TUBULAR DEVICE AND INFLATABLE HEAD HARNESS FOR AIRCRAFT BREATHING MASK

(75) Inventors: Laurent Dussart, Saulx-les-Chartreux (FR); Remy Schoettel, Saint Vit (FR); Vincent Greter, Elancourt (FR)

(73) Assignee: Zodiac Aerotechnics, Plaisir (FR)

( * ) Notice: Subject to any disclaimer, the term of this patent is extended or adjusted under 35 U.S.C. 154(b) by 691 days.

(21) Appl. No.: 12/922,860

(22) PCT Filed: Mar. 19, 2008

(86) PCT No.: PCT/IB2008/052205

§ 371 (c)(1), (2), (4) Date: Sep. 16, 2010

(87) PCT Pub. No.: WO2009/115868

PCT Pub. Date: Sep. 24, 2009

(65) Prior Publication Data

US 2011/0011405 A1 Jan. 20, 2011

(51) Int. Cl.

*A62B 18/08* (2006.01)
*A61M 16/00* (2006.01)

(52) U.S. Cl.

CPC .................................... *A62B 18/084* (2013.01)

(58) Field of Classification Search

USPC ............. 128/207.11, 206.21, 206.23–206.28, 128/207.13

See application file for complete search history.

(56) References Cited

U.S. PATENT DOCUMENTS

| | | | | |
|---|---|---|---|---|
| 3,599,636 | A | 8/1971 | Gutman et al. | |
| 4,437,462 | A | 3/1984 | Piljay et al. | |
| 4,729,765 | A * | 3/1988 | Eckels et al. | 604/540 |
| 5,269,296 | A * | 12/1993 | Landis | 128/207.18 |
| 5,640,951 | A * | 6/1997 | Huddart et al. | 128/204.17 |
| 3,000,530 | A1 | 1/2003 | McDonald et al. | |
| 8,100,127 | B2 * | 1/2012 | Worley | 128/207.14 |
| 2002/0108614 | A1 * | 8/2002 | Schultz | 128/207.14 |
| 2007/0012317 | A1 * | 1/2007 | Flagler et al. | 128/207.14 |
| 2008/0060649 | A1 * | 3/2008 | Veliss et al. | 128/205.25 |
| 2008/0099023 | A1 * | 5/2008 | Berthon-Jones | 128/206.24 |
| 2008/0230067 | A1 * | 9/2008 | Kwok et al. | 128/206.24 |

FOREIGN PATENT DOCUMENTS

DE 3608668 9/1987

* cited by examiner

*Primary Examiner* — Rachel Young

(74) *Attorney, Agent, or Firm* — Kilpatrick Townsend & Stockton LLP

(57) ABSTRACT

Described are elastic tubular devices including an inner tube (23) made of an elastic and gas impermeable material; and a sheath (21) surrounding the inner tube and made of a woven cloth of flame resistant meta-aramid yarns, wherein the tubular device has a longitudinal extension of at least approximately 1.4 when inflated by a gas having a pressure of at least approximately 0.5 bar.

20 Claims, 2 Drawing Sheets

ELASTIC TUBULAR DEVICE AND INFLATABLE HEAD HARNESS FOR AIRCRAFT BREATHING MASK

CROSS REFERENCE TO RELATED APPLICATION

This application is the U.S. national phase of International Application No. PCT/IB2008/052205 filed on Mar. 19, 2008, and published in English as International Publication No. WO2009/115868 A1 on Sep. 24, 2009, the entire contents of which are incorporated herein by reference.

FIELD OF THE INVENTION

The invention relates to an elastic tubular device and an inflatable head harness for aircraft breathing mask which used the same.

BACKGROUND OF THE INVENTION

The respiratory mask typically worn by aircraft crewmembers must be attached surely and rapidly on the crewmember head. And it must be attached on an one-handed basis, since the user's other hand is frequently occupied in some other essential task.

For example, if because of a pressurization failure, the pilot of an aircraft is required rapidly to don his respiratory mask to provide the necessary oxygen for breathing, he often must do so with one hand while his other hand is occupied in controlling the aircraft. Thus, the use of an inflatable head harness has been suggested in order to permit the respiratory mask to be donned using only one hand. The head harness is expanded diametrically by the introduction of pressurized gas to cause the harness to increase in size so that it can be positioned over the head of the user. The gas flow is controlled by a valve attached to the respiratory mask, and, after enlargement, the respiratory mask is placed in position over the nose and mouth, with the head harness extended over and spaced from the back of the head. Once the respiratory mask has been properly positioned, the pressure in the head harness is released, causing the harness to contract and to contact the head of the pilot, whereby the respiratory mask is securely held in its proper position. Meanwhile, the pilot's other hand is free to control the aircraft or to perform such other tasks as may be required.

An inflatable head harness is shown and described in U.S. Pat. No. 3,599,636 in which the harness is defined by a pair of spaced, expandable rubber tubes which are housed within an outer casing of material which has limited yieldability and which is initially in pleated form.

The disclosed harness needs to work a minimum pressure of 6 bars at the arrival of breathing gas.

However, more and more often, the breathing gas supply system of aircraft uses Onboard Oxygen Generating System, or OBOGS, which delivers breathing gas at a maximum pressure of 4 to 5 bars. This pressure is not sufficient to inflate correctly the usual inflatable harness for allowing the crewmember to install the mask easily.

Therefore, there is a need for an apparatus which allows the use of inflatable harness with the pressure level delivered by OBOGS.

SUMMARY OF THE INVENTION

To better address one or more concerns, in a first aspect of the invention, an elastic tubular device comprising:

- an inner tube made of an elastic and gas impermeable material; and,
- an sheath surrounding the inner tube and made of a woven cloth of flame resistant meta-aramid yarns, wherein the tubular device has a longitudinal extension of at least approximately 1.4 when inflated by a gas having a pressure of at least approximately 0.5 bar.

The tubular device has advantageously the same longitudinal extension ratio than a standard tubular device for inflatable harness but this extension ratio is achieved with a pressure level which can be obtained from OBOGS.

In particular embodiments,

- the tubular device has a longitudinal extension of at least approximately 1.5 when inflated by a gas having a pressure of at least approximately 0.7 bar.
- the inner tube is molded in silicon material, said silicon having a hardness of less than 75 shore A, and Young's modulus of less than 200 MPa.
- said silicon has a hardness of less than 35 shore A.
- internal diameter of the inner tube is at least approximately 17 millimeters.
- the sheath is woven so that its longitudinal stretch ratio is approximately 3.

In another aspect of the invention, a breathing mask for aircraft comprises an inflatable harness composed of elastic tubular devices as disclosed hereabove.

Therefore, the user may advantageously inflate the harness with the pressure level achieved by OBOGS to don the breathing mask using only one hand.

In particular embodiment of the breathing mask:

- the tubular devices are connected to a gas source through nozzles, said nozzles comprising a cylindrical cover which gets wider in the direction of the tubular devices.
- the ends of the inner tube of said tubular devices are fixed inside the cylindrical cover are thicker than the other part of the inner tube.

Depending on the type of the breathing mask and tubular device, a particular embodiment may be preferred as easier to adapt. Aspects of these particular embodiments may be combined or modified as appropriate or desired, however.

BRIEF DESCRIPTION OF THE DRAWINGS

These and other aspects of the invention will be apparent from and elucidated with reference to the embodiment described hereafter where.

DESCRIPTION OF EMBODIMENTS OF THE INVENTION

Figure 1:
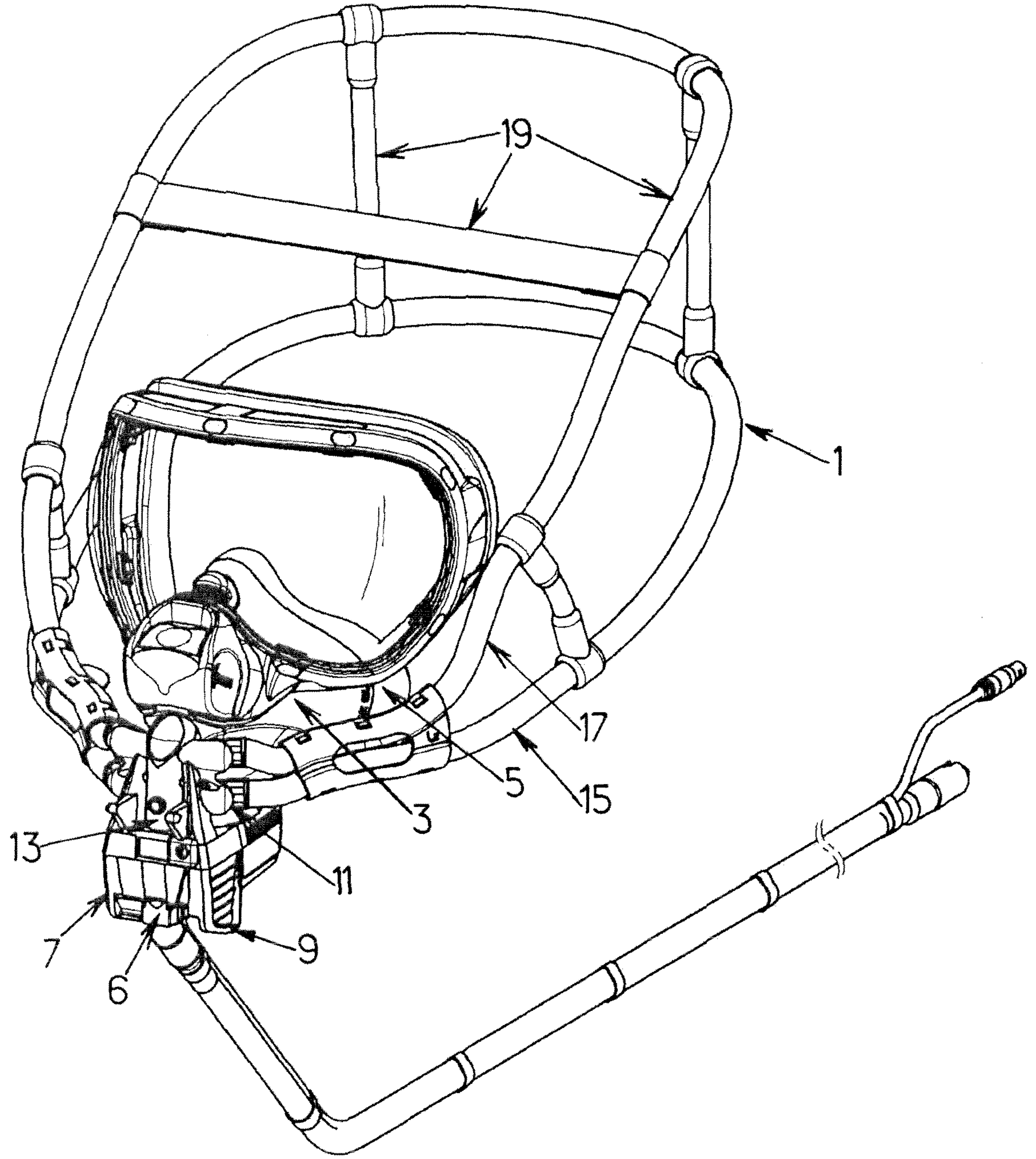
FIG. 1 is an isometric view of a breathing mask with its inflatable harness according to an embodiment of the invention.

In reference to FIG. 1, a head harness 1 is utilized in conjunction with a respiratory mask 3 of the type intended to provide oxygen to aircraft crewmembers under high altitude conditions or under conditions in which the aircraft cabin pressurization has for some reason been lost.

Mask 3 includes a flexible, generally cup-shaped face member 5 adapted to fit over and cover the mouth and nose of the user, and which is suitably shaped to provide a comfortable fit.

Positioned at the forward outer end of face member 3 is a control valve 6 having a slidable valve member 7, 9 positioned on each side of control valve 5, each of which is adapted to selectively open and close a passage way to admit a pressurized fluid to the harness structure, all will hereinafter be described. Control valve 6 can be a two-position valve, wherein in one position it permits communication between the head harness and the atmosphere while it simultaneously prevents the entry of pressurized gas to the harness structure. As it is apparent, control valve 6 is adapted for one-handed use, thereby permitting the other hand of the user to be occupied with other tasks. Although a specific structure of control valve is shown and described, it will be apparent to those skilled in the art that other types of control valve structure could be successfully utilized together with the head harness structure of the invention, and the control valve structure shown is for illustrative purposes only.

Control valve 6 includes a valve housing 11, which fits over and is secured to forward position 13 of face member 3, and to which is attached two tubular members 15, 17, each tubular member having the form of a loop, each end of which is securely received in housing in substantially gas-tight relationship. Tubular members 15, 17 are adapted to encircle the head of the user and, when properly positioned they securely hold face member 3 in its operative position. Space members 19 are positioned there between to hold tubular elements 15, 17 in a predetermined, spaced angular relationship relative to each other for maximum comfort on the part of the user.

Figure 2:
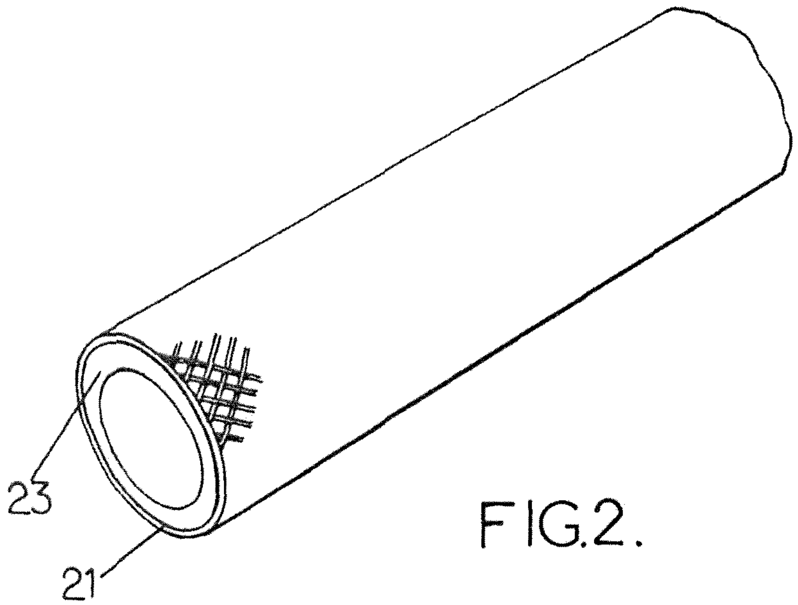
FIG. 2 is an isometric view of a portion of a tube used in the harness of of FIG. 1.

Tubular members 15, 17 include, FIG. 2, a first, outer tube 21, or sheath, and a second, inner tube 23. Outer tube 21 is made from an elastic material which is elastically extensible in an axial or longitudinal direction, but which need not be elastically extensible in a radial or transverse direction. The purpose of the longitudinal extensibility is to permit axial extension of tubular members 15, 17 to enable their placement over the head of the user, and subsequently to permit it to contract into closely fitting engagement with the user's head to hold the device to which it is applied on its proper position. A preferred material from which outer tube 21 can be formed is a woven cloth composed of flame resistant meta-aramid yarn such as NOMEX (trademark of Dupont Inc.) fiber. The NOMEX has the advantage to have a good heat resistance compatible with aircraft regulation, a great mechanical resistance and particularly to defibering, and a homogeneous sliding between fibers which guarantee a homogeneous elongation of the tubular members.

Inner tube 23 fits completely within outer tube 21 and is formed from a fluid impermeable and elastic material, preferably a silicone-type material. Typically, inner tube 23 is a silicone molded tube.

Therefore, the inner tube 23, being fluid impermeable and elastic, is used to transform the breathing gas pressure into a mechanical increase of the tubular members length and the outer tube 21 is used to protect the inner tube 23 from aggressive contact and to direct the force generated by the breathing gas pressure to the longitudinal extension of the tubular members.

Figure 3:
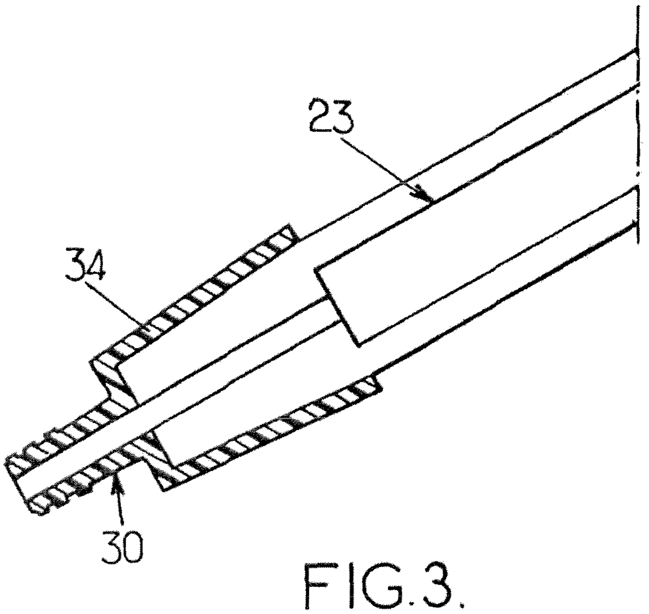
FIG. 3 is a section view of a connection of the tube of FIG. 2 with the breathing mask of FIG. 1.

The tubular members 15, 17 are connected to the valve housing 11 by means of nozzles 30, FIG. 3.

The nozzle comprises a cylindrical cover 34 which gets wider in the direction of the tubular members to spread constraints generated by inflating the harness.

The end of the inner tube 23 is fixed inside the cylindrical cover 34 and is thicker than the other part of the tube also to spread constraints.

The breathing gas generated by OBOGS has a pressure as low as 0.7 bars and a maximum flow rate of around 85 l/min.

The tube needs to elongate by a factor of around 1.5 to allow the user's head to position into the harness, whatever the head size is.

However, it may be acceptable that the tube elongates by a factor or only 1.4 if the pressure delivered by OBOGS is only 0.5 bars.

To offer a good comfort to the user while maintaining closely in place the breathing mask, the harness needs to squeeze the head, when deflated, with strength of more than 20 Newton.

With a pressure of 0.7 bars and considering the silicone elasticity, it appears that the inner diameter of the tube needs to be around 18 mm.

Knowing the silicone elasticity and the elongation ratio, the man skilled in the art determines the requested silicone section which, with the inner diameter, gives the thickness.

In order to have a silicone thickness with a good protection against puncture, the silicone is chosen advantageously among those having a hardness of less than 75 shore A, preferably less than 35 shore A, and a Young's modulus of less than 200 MPa.

To obtain the correct longitudinal extensibility of 1.5, and to protect against a puncture due to an overpressure, for instance, of 9 bars, the number of spindles and the weaving angle are advantageously adjusted during the weaving of the outer tube to achieve a longitudinal stretch ratio of the outer tube alone of 3. To calculate the longitudinal stretch ratio, the outer tube is considered by itself, without the inner tube and the comparison is done between the outer tube stretched longitudinally and the outer tube in a rest position which means it has a diameter of approximately 20 mm, i.e. the outer diameter of the inner tube.

Other variation to the disclosed embodiments can be understood and effected by those skilled in the art in practicing the claimed invention, from a study of the drawings, the disclosure and the appended claims. In the claims, the word "comprising does not exclude other elements, and the indefinite article "a" or "an" does not exclude a plurality.

The invention claimed is:

1. A breathing mask for aircraft comprising an inflatable harness composed of at least one elastic tubular device, each elastic tubular device comprising:

an inner tube made of an elastic and gas impermeable material; and a sheath surrounding the inner tube and made of a woven cloth of flame resistant meta-aramid yarns, wherein the tubular device has a longitudinal extension of at least 1.4 when inflated by a gas having a pressure of 0.5 bar.

2. The breathing mask according to claim 1, wherein the tubular device has a longitudinal extension of at least 1.5 when inflated by a gas having a pressure of 0.7 bar.

3. The breathing mask according to claim 1, wherein the inner tube is molded in silicon material.

4. The breathing mask according to claim 1, wherein said sheath is woven so that its longitudinal stretch ratio is approximately 3.

5. The breathing mask according to claim 1, wherein said tubular device is connected to a gas source through nozzles, said nozzles comprising a cylindrical cover which gets wider in the direction of the tubular device.

6. The breathing mask according to claim 1, wherein the inner tube fits completely within the sheath when not inflated.

7. The breathing mask according to claim 1, wherein the inner tube of said tubular device has at least one end portion fixed inside a cylindrical cover and an extensible portion away from the cylindrical cover, the end portion is thicker than the extensible portion of the inner tube, said end portion of the inner tube having an external surface flush with an external surface of said extensible portion of the inner tube.

8. The breathing mask according to claim 1, wherein the inner tube of said tubular device has at least one portion fixed inside a cylindrical cover and an extensible portion, at least most of the inner tube which is inside the cylindrical cover has an internal cross section smaller than the internal cross section of said extensible portion of the inner tube.

9. A breathing mask for aircraft comprising an inflatable harness composed of at least one elastic tubular device, each elastic tubular device comprising:

an inner tube made of an elastic and gas impermeable material; and a sheath surrounding the inner tube and made of a woven cloth of flame resistant meta-aramid yarns, wherein the tubular device has a longitudinal extension of at least 1.4 when inflated by a gas having a pressure of 0.5 bar, and the inner tube is molded in silicon material having a hardness of less than 75 shore A, and Young's modulus of less than 200 MPa.

10. The breathing mask according to claim 9, wherein said silicon has a hardness of less than 35 shore A.

11. The breathing mask according to claim 9, wherein an internal diameter of the inner tube is at least 17 millimeters.

12. The breathing mask according to claim 9, wherein the inner tube of said tubular device has at least one end portion fixed inside a cylindrical cover and an extensible portion directly connected to said end portion, the end portion is thicker than the extensible portion of the inner tube, said end portion of the inner tube having an internal cross section smaller than an internal cross section of said extensible portion of the inner tube.

13. The breathing mask according to claim 9, wherein the inner tube of said tubular device has at least one end portion fixed inside a cylindrical cover and an extensible portion away from the cylindrical cover, the end portion is thicker than the extensible portion of the inner tube, said end portion of the inner tube having an external surface flush with an external surface of said extensible portion of the inner tube.

14. The breathing mask according to claim 9, wherein said tubular device is connected to a gas source through nozzles, said nozzles comprising a cylindrical cover which gets wider in the direction of the tubular device.

15. A breathing mask for aircraft comprising an inflatable harness composed of at least one elastic tubular device, each elastic tubular device comprising:

an inner tube made of an elastic and gas impermeable material; and a sheath surrounding the inner tube and made of a woven cloth of flame resistant meta-aramid yarns, wherein the tubular device has a longitudinal extension of at least 1.4 when inflated by a gas having a pressure of 0.5 bar, and an internal diameter of the inner tube is at least 17 millimeters.

16. The breathing mask according to claim 15, wherein the inner tube of said tubular device has at least one end portion fixed inside a cylindrical cover and an extensible portion directly connected to said end portion, the end portion is thicker than the extensible portion of the inner tube, said end portion of the inner tube having an internal cross section smaller than an internal cross section of said the extensible portion of the inner tube.

17. The breathing mask according to claim 15, wherein ends of the inner tube of said tubular device are fixed inside a cylindrical cover and are thicker than another part of the inner tube, said ends of the inner tube having an external cross section identical to an external cross section of said other part of the inner tube.

18. The breathing mask according to claim 15, wherein said tubular device is connected to a gas source through nozzles, said nozzles comprising a cylindrical cover which gets wider in the direction of the tubular device.

19. A breathing mask for aircraft comprising an inflatable harness composed of at least one elastic tubular device, each elastic tubular device comprising:

an inner tube made of an elastic and gas impermeable material; and a sheath surrounding the inner tube and made of a woven cloth of flame resistant meta-aramid yarns, wherein the tubular device has a longitudinal extension of at least 1.4 when inflated by a gas having a pressure of 0.5 bar, and the inner tube of said tubular device has at least one end portion fixed inside a cylindrical cover and an extensible portion directly connected to said end portion, the end portion is thicker than the extensible portion of the inner tube, said end portion of the inner tube having an internal cross section smaller than an internal cross section of said extensible portion of the inner tube.

20. The breathing mask according to claim 19, wherein said tubular device is connected to a gas source through nozzles, said nozzles comprising a cylindrical cover which gets wider in the direction of the tubular device.

* * * * *